United States Patent [19]
Terstappen et al.

[11] Patent Number: 5,646,001
[45] Date of Patent: Jul. 8, 1997

[54] AFFINITY-BINDING SEPARATION AND RELEASE OF ONE OR MORE SELECTED SUBSET OF BIOLOGICAL ENTITIES FROM A MIXED POPULATION THEREOF

[75] Inventors: Leon W. M. M. Terstappen, Huntingdon Valley, Pa.; Galla C. Rao, Princeton, N.J.; Dhanesh I. Gohel, Levittown, Pa.; Brian P. Feeley, Easton, Pa.; Steven Gross, Ambler, Pa.; Ellen S. Church, Trenton, N.J.; Paul A. Liberti, Huntington Valley, Pa.

[73] Assignee: Immunivest Corporation, Wilmington, Del.

[21] Appl. No.: 395,967

[22] Filed: Feb. 28, 1995

Related U.S. Application Data

[63] Continuation-in-part of Ser. No. 6,071, Jan. 15, 1993, Pat. No. 5,466,574, which is a continuation-in-part of Ser. No. 674,678, Mar. 25, 1991, Pat. No. 5,186,827.

[51] Int. Cl.$^6$ ............................. G01N 33/567
[52] U.S. Cl. ............ 435/7.21; 435/5; 435/7.2; 435/7.32; 435/7.92; 435/239; 435/243; 435/962; 435/973; 436/526; 436/532; 436/533; 436/63; 436/174; 436/824; 436/825; 209/213; 210/222; 210/695
[58] Field of Search .................. 435/5, 7.2, 7.21, 435/7.32, 7.92, 239, 240.1, 243, 962, 973; 436/518, 526, 532, 533, 63, 174, 824, 825; 209/213; 210/222, 695

[56] References Cited

U.S. PATENT DOCUMENTS

| 3,970,518 | 7/1976 | Giaever | 435/239 |
| 4,018,886 | 4/1977 | Giaever | 436/526 |
| 4,230,685 | 10/1980 | Senyei et al. | 436/526 |
| 4,267,234 | 5/1981 | Rembaum | 428/403 |

(List continued on next page.)

FOREIGN PATENT DOCUMENTS

| 22948/88 | 4/1989 | Australia. |
| 463508A1 | 6/1991 | European Pat. Off. . |

(List continued on next page.)

OTHER PUBLICATIONS

Chen and Gold, "Selection of High-Affinity RNA Ligands to Reverse Transcriptase: Inhibition of cDNA Synthesis and RNase H Activity", Biochemistry, 33:8746–8756 (1994).

Clark, N.W.T. et al., "Positive and Negative Selection of Cells by Hapten-Modified Antibodies", J. Immunol. Method., 51: 167–70 (1982).

(List continued on next page.)

Primary Examiner—James C. Housel
Assistant Examiner—Susan Wolski
Attorney, Agent, or Firm—Dann, Dorfman, Herrell and Skillman

[57] ABSTRACT

A method for separation of a mixture of biological entities into at least three distinct, subpopulations. Different antibodies are provided, with each antibody bound to a solid support in a unique manner such that by a manipulation of the physical or chemical environment, the bonds between the antibodies and the solid supports can be selectively broken. The mixed population of cells is incubated with the antibodies. The cells are magnetically separated from a test medium and collected in a monolayer upon a collection surface. Then by manipulation of the physicochemical environment, specific linkages can be broken and desired cell subpopulations released from the collection surface. This method has medically significant diagnostic and therapeutic applications, as entire cell types can be separated from non-malignant medically vital cell types. Cancer can be diagnosed, staged, and monitored. Genetic analysis from maternal blood, CVS, or amniocentesis samples is possible. Diseases such as AIDS, tuberculosis or hepatitis can be monitored. This invention also has utility in the fields of bone marrow transplantation, fetal cell research, in vitro fertilization, and gene therapy.

38 Claims, 4 Drawing Sheets

U.S. PATENT DOCUMENTS

| | | | |
|---|---|---|---|
| 4,452,773 | 6/1984 | Molday | 424/1.37 |
| 4,554,088 | 11/1985 | Whitehead et al. | 252/62.54 |
| 4,659,678 | 4/1987 | Forrest et al. | 436/512 |
| 4,795,698 | 1/1989 | Owen et al. | 435/4 |
| 4,988,621 | 1/1991 | Ruoslahti et al. | 435/24.02 |
| 5,081,030 | 1/1992 | Civin | 435/240.2 |
| 5,186,827 | 2/1993 | Liberti et al. | 210/222 |
| 5,200,084 | 4/1993 | Liberti et al. | 210/695 |
| 5,385,707 | 1/1995 | Miltenyi et al. | 422/69 |
| 5,466,574 | 11/1995 | Liberti et al. | 435/5 |

FOREIGN PATENT DOCUMENTS

| | | |
|---|---|---|
| WO9102811 | 3/1991 | WIPO . |
| WO9116452 | 10/1991 | WIPO . |
| WO92/00091 | 1/1992 | WIPO . |
| WO9402016 | 2/1994 | WIPO . |
| WO9415696 | 7/1994 | WIPO . |
| WO9420858 | 9/1994 | WIPO . |
| WO9425852 | 10/1994 | WIPO . |

OTHER PUBLICATIONS de Kruif, John et al., "Selection and Application of Human scFv Antibody Fragments from a Semisynthetic Phage Antibody Display Library with 'Designed' CDR3 Regions", Proc. Natl. Acad. Sci. USA, 92: 3938–3942 (1995).

de Kruif, John et al., "Rapid Selection of Cell Subpopulation–specific Human Monoclonal Antibodies from a Synthetic Phage Antibody Library", J. Mol. Biol., 248: 97–105 (1995).

Fodor, Stephen P.A. et al., "Light–Directed, Spatially Addressable Parallel Chemical Synthesis", Science, 251: 767–773 (1991).

Geretti, A.M. et al., "Preservation of Phenotype and Function of Positively Selected Virus–Specific CD8+ T Lymphocytes Following Anti–Fab Detachement from Immunomagnetic Beads", J. Immunol. Meth., 161: 129–133 (1993).

McCafferty, John et al., "Phage Antibodies: Filamentous Phage Displaying Antibody Variable Domains", Nature, 348: 552–554 (1990).

Rasmussen, A.–M. et al., "A New Method for Detachment of Dynabeads from Positively Selected B Lymphocytes", J. Immunol. Meth., 146: 195–202 (1992).

Robinson, P. et al., "The Properties of Magnetic Supports in Relation to Immobilized Enzyme Reactors", Biotech. Bioeng., XV: 603–606 (1973).

Scouten, William H. et al., "Reversible Immobilization of Antibodies on Magnetic Beads", Anal. Biochem., 205: 313–318 (1992).

Dynal, DETACHaBEAD product literature.

AFFINITY-BINDING SEPARATION AND RELEASE OF ONE OR MORE SELECTED SUBSET OF BIOLOGICAL ENTITIES FROM A MIXED POPULATION THEREOF

RELATED INVENTIONS

This is a continuation-in-part of patent application Ser. No. 08/006,071, filed Jan. 15, 1993 now U.S. Pat. No. 5,466,574, which is a continuation-in-part of patent application Ser. No. 674,678, filed Mar. 25, 1991, now U.S. Pat. No. 5,186,827, which are commonly owned with the present application and which are incorporated by reference in the present application as if set forth herein in full.

FIELD OF THE INVENTION

The present invention relates to affinity-binding separation of a mixed population of biological entities in which the method of capture is performed such that it is possible to selectively release a distinct subset of biological entities, or several such subsets in sequence, from the captured population by controlled dissociation from the capture agent. This invention has utility in the fields of diagnostic and therapeutic medicine, genetic manipulation, in-vitro fertilization, forensic science, food and environmental testing, and scientific research.

BACKGROUND OF THE INVENTION

Separation technology has evolved over centuries and is extensively applied in numerous industries, including such basic techniques as winnowing grain from chaff. Low cost separation processes are based on differences in gross physical properties, e.g., size, shape, density, oil/water solubility, and utilize a variety of physical forces or barriers such as gravity, centrifugation, flotation and sieving. More demanding separations are based on chemical and/or physicochemical properties which function at the molecular level, such as charge density and molecular size and shape. When entities are virtually identical at the gross and molecular level, affinity-binding is often relied on as the basis for separation. Affinity-binding discriminates at the molecular level, via a molecular "lock & key" mechanism, which is commonly referred to as a specific binding pair, e.g. ligand/receptor, interaction. The immune system in which antibodies and/or cells attack and destroy specific pathogens, as well as the endocrine system, in which hormones secreted by one gland create physiological effects in target tissue elsewhere in the body, are examples of nature's use of the affinity-binding principle.

Affinity-binding technology often makes use of receptors such as polyclonal antibodies and lectins, as well as hapten-labeling of molecules for recognition by anti-haptens. The emergence of monoclonal antibody technology has made affinity-binding separations a cost-effective and efficient reality. The next generation of affinity-binding technology will likely include the use of single chain antibodies, peptides and oligonucleotides or a combination thereof. Single chain antibodies (scFv) are engineered proteins which may be expressed on the surface of phages such as M13 or fd, and which bind to antigenic determinants in a manner similar to monoclonal antibodies which are traditionally generated from hybridomas. Relatively short peptides can also contain a binding site capable of discriminating antigenic determinants and can be further linked to small immuno-specifically recognizable substances, which effectively replace the "conserved" region of an antibody, and thus can themselves be immuno-specifically bound using a "second antibody" capture technique. Oligonucleotides may be chemically conjugated to either peptides or small molecules, and the resulting conjugate can specifically bind to antigenic determinants. In other cases, the oligonucleotide alone can bind to an antigenic determinant with high specificity. In order to obtain the desired specificity of these antigen binding probes, libraries have been constructed which contain a large diversity of such probes. Antigen binding probes can be isolated from such libraries by presentation of the appropriate antigen. After isolation of the antigen binding probes with the desired specificity, the probe can be further characterized and large quantities can be produced. See, for example, De Kruif, et al., *PNAS* in press; De Kruif, et al., *JMB*, in press; Chen & Gold, *Biochemistry*, 33(29):8746–56 (1994); Fodor, et al., *Science*, 251:767–73 (1991); and McCafferty, *Nature*, 348:552–54 (1990).

Separations using affinity-binding techniques are well established. There are numerous procedures available for separating biological entities such as cells, cell organelles and other cell components, viruses, bacteria, proteins and polynucleotides. Many of these procedures are dependent on transient binding of a target substance to a receptor on a solid support. Affinity-binding separation is commonly used in the purification of antibodies. Many commercially available affinity chromatography systems use polymeric beads linked to protein A or G, which specifically bind antibody, releasing the antibody upon flushing the column with low pH buffers. Other affinity-binding systems capture biological molecules, only to release the captured substance upon the introduction of another substance which can displace the entity from the support via competitive binding. Ionic strength manipulation may also be used to remove a specifically bound substance from an affinity separation device, such as a column.

Historically, binding agents having specific binding affinity for various analytes, e.g., antigens or antibodies, were attached to a solid support such as a beaker or a micro-titre plate, and placed in contact with the test sample, after which the unbound sample components were physically removed, thereby capturing the analyte of interest from the test medium. Other stationary supports include test tubes, membranes, gels and filter media. Mobile solid supports, such as latex beads, or beads made from other polymeric material are widely used to provide increased surface area on which to anchor a specific binding substance. Magnetic particles are advantageously used to facilitate separations. Magnetic particles ranging in size from 0.01–6 microns have been described in the patent literature, including, by way of example, U.S. Pat. Nos. 3,970,518; 4,018,886; 4,230,685; 4,267,234; 4,452,773; 4,554,088; 4,659,678 and 4,795,698. Relatively large magnetic particles, such as the 4.5 micron sized particles marketed by Dynal (Oslo, Norway) respond to weak magnetic fields and magnetic gradients and are used for many types of biological separations. Because of their size, such particles tend to settle rapidly from solution and also have limited surface area per unit weight. Larger magnetic particles also tend to aggregate after they have been subjected to a magnetic field for a variety of reasons. Smaller sized magnetic particles, on the order of 0.01–0.8 microns, generally fall into two broad categories. The first category includes particles that are permanently magnetized and the second includes particles that are magnetically responsive only when subjected to a magnetic field. The latter are sometimes referred to as superparamagnetic particles. However, certain ferromagnetic materials, e.g., magnetic iron oxide, may be characterized as superparamagnetic when the crystal size is about 30 nm or less in diameter. Larger crystals of ferromagnetic materials, by contrast, retain permanent magnetic characteristics after exposure to a magnetic field and tend to aggregate thereafter. See P. Robinson, et al., *Biotech Bioeng*, XV:603–06 (1973).

Various methods have been proposed to effect the release of cells or other target substances from a solid support once they have been separated. Giaever (U.S. Pat. No. 3,970,518) discloses the use of antibody-coated magnetic microspheres to separate cells, but uses a chemical cleaving agent such as formic or sulfuric acids to release the separated cells. Hayman, et al. (U.S. Pat. No. 4,988,621) discloses the use of a short peptide which interferes with the binding of cells to fibronectin, allowing the detachment of cells from a solid support. Mori (EP 463508 A) discloses the use of a temperature-responsive adhesive to immobilize a cell for microinjection, lowering the temperature to release the immobilized cell. Berenson (WO 91/16452) describes a technique involving agitation of an avidin column to remove cells captured thereon. The use of ionic strength manipulation to reversibly immobilize antibodies bound to magnetic beads has also been reported. See, for example, Scouten, *Anal. Biochem.* 205:313–18 (1992). Civin (U.S. Pat. No. 5,081,030) discloses the use of chymopapain to digest the cell surface antigen My 10, releasing stem cells from magnetic particles used to isolate the stem cells from a cell suspension. Berge et al. (WO 94/20858) describes the separation of target substances by means of a relatively large magnetic particle linked via a hydroxyboryl/cis-diol bond to an antibody, which bond is cleaved after separation of the target substance. The commercially available DETACHa-BEAD from Dynal (Oslo, Norway) comprises an anti-mouse FAb with higher affinity for the binding site of a monoclonal antibody than the monoclonal has for its corresponding antigen. Therefore, the anti-FAb antibody can displace the original MAb from a target cell. See Geretti, et al. *J. Immunol. Meth.* 161:129–31 (1993); and Rasmussen, et al., *J. Immunol. Meth.* 146:195–202 (1992). Kessler (WO 94/02016) describes the use of an excess of soluble hapten to disrupt a hapten-antihapten complex, thereby releasing a cell from its solid support. See also Clark et al., *J. Immunol. Meth.*, 51:167–70 (1982).

All of the above are generally satisfactory methods for the separation of a target substance from non-target substances, but the methods lack the capability to separate a selected subset of biological entities, or several selected subsets in sequence, from a bound mixed population thereof. Currently available biological separation technology enables only the separation or removal of a single target substance, leaving various non-target substances behind (positive selection), or the removal of various non-target substances, leaving a single target substance behind (negative selection). Such existing separation techniques are thus limited to the separation of a mixed population of biological entities into essentially two groups, target and non-target. There are certain drawbacks inherent in using a series of positive selection separations to separate more than one class of target substance from a mixture containing several non-target substances, based on existing separation techniques. Each interaction of biological entity with a specific receptor requires a finite time to reach equilibrium. Moreover, each step involved in such a separation is accompanied with variable degrees of loss of target entities and capture of non-target entities, no matter what type of specific procedure is employed. The time demands, and associated expense of multiple incubations, separations and restoration of the separation apparatus for each subsequent selection are also not insignificant. A technically feasible, economic technique for isolating one or more selected target substances from a mixed population thereof remains a highly desired goal which has not yet been satisfactorily realized.

Multi-parameter separations have been achieved in the last decade with the advent of fluorescent activated cell sorting. Cells are passed individually through a measurement orifice by means of hydrodynamic focusing. A light beam (such as a laser) is focused on the cell stream and the light absorbed, scattered or emitted is measured from each passing cell event. Various parameters can be measured of each cell passed through the orifice, including forward light scatter (a measure of cell size), orthogonal light scatter (a measure of cell granularity), depolarized light scattering (a measure of large intra cellular granules) and fluorescence. The fluorescent signals which can be potentially measured depend on the fluorescent probe, the wavelength(s) of the laser(s) and the spectral separation of the fluorescent probes used. Monoclonal antibodies specific for different antigens can be labeled with fluorochromes which can be spectrally separated and cells exhibiting different combinations of these cell surface antigens can thus be discriminated from each other. After identification of the cells, they can be separated by either mechanical separation or more conventionally by deflection of charged droplets which contain the cells with desired specificity. Although flow cytometry is an extremely powerful tool to identify and select cell subpopulations from a mixture of cells with a high degree of certainty, flow cytometers are limited by software and hardware requirements related to the passage of single cells. The highest reported cell rate which can be processed via flow cytometry is 40,000 cells/second, although commercially available instruments typically function at a speed which is ten-fold lower. See, Shapiro, Practical Flow Cytometry, Chapters 3 and 6 (1995). Additionally, cell loss can be significant, and as cell purity increases, the cell loss further increases. Furthermore, only two populations can be separated by a flow cytometer at a time, so that sorting cells into more than two populations requires multiple runs through the cytometer further exacerbating the cell loss. The complexity of these instruments also makes them expensive to acquire and maintain. The only practical option available to those interested in using flow cytometry appears to be the removal of the bulk of cells, then using flow cytometers to analyze the remaining portion of cells. This is the approach taken, for example, by Bolton, et al (WO 94/25852) with the removal of 95% of the leukocytes from a solid tumor sample with CD45 antibody. Although this approach overcomes the above-noted limitations of flow cytometers with respect to throughput, a more economical procedure enabling the separation of cells en masse is still a desired objective for various applications in scientific research, environmental analysis, food testing, forensic science, but most importantly in the medical field for the separation of different types of cells for diagnostic and therapeutic purposes, including gene therapy.

SUMMARY OF THE INVENTION

According to one aspect of the present invention, a method is provided for isolating a selected subset of biological entities from among a plurality of subsets in a mixed population of biological entities, which comprises a first subset having a first characteristic determinant and at least one other subset having at least a second characteristic determinant, one of the last-mentioned subsets being the selected subset. A plurality of capture agents is provided, such that each capture agent comprises a receptor attached to a solid support. Included in the plurality of capture agents is a first capture agent comprising a receptor which specifically binds, either directly or indirectly, to the characteristic determinant of the first subset, and at least a second capture agent comprising a receptor which specifically binds, either directly or indirectly, to the characteristic determinant of at least one other subset, the subset to which each capture agent binds being the target subset of each capture agent. A test sample of the mixed population of biological entities is contacted with the plurality of capture agents, whereby the receptor of the first capture agent specifically binds to the first subset and the receptor of the second capture agent specifically binds to at least one other subset, with at least one of the first and second capture agents being dissociably bound to its respective target subset. The bound subsets are next separated from the test sample and any subset of the population that is not bound to a capture agent. One of the dissociably bound subsets is thereafter dissociated from the capture agent to which it is bound and then isolated.

The isolated, selected subset is normally recovered for further analysis and/or propagation.

The dissociation and isolation steps of the above-described method may be repeated to yield a second or third selected subset, and so on, if desired, provided that the bond linking one capture agent to a selected target subset is differentially dissociable from the bond linking each other capture agent to its respective, selected target subset, such that dissociation of the one capture agent from its target subset will not result in dissociation of another capture agent from its selected target subset.

In accordance with another aspect of this invention, a composition of capture agents is provided for use in performing the method of the invention summarized above.

According to a further aspect of the invention, a test kit is provided for use in facilitating the isolation and analysis of specific cell types, e.g., fetal cells present in maternal blood.

The single separation of a plurality of subsets within a mixed population of biological entities, followed by the release of one or more individual, selected subsets of interest is substantially more efficient than multiple selections, each with a single release, because less effort is involved in breaking bonds, as opposed to forming bonds. Moreover, there are generally more ways to control the breakage of bonds than to control the formation of bonds. This superiority of dissociative chemistry is evident in column chromatography wherein various substances are bound to columns and sequentially released as different elution buffers are passed through the column.

The method of the invention involves a unique set of operating parameters which enable the successful performance of biological and other separations not heretofore attainable. In conventional affinity separation, wherein a ligand is attached directly to a stationary solid support, such as in affinity chromatography, capture and separation of the target substance are simultaneous events. For separations using a particulate magnetic capture agent, as in the preferred embodiments of the present invention, these two events are entirely separate. The bifurcation of these two events according to a preferred embodiment of this invention affords significant advantages. In the method of the invention, affinity-binding reactions are coupled with respective specific cleavage reaction. Thus, by creating affinity-binding/cleavage pairs, two distinct specificities for each separation procedure result. When it is desired to separate one or more selected subset of biological entity from a mixed population of such entities on a collection surface, this additional parameter allows permutations of events, such that separations which were either difficult or impossible, can now be done with relative ease.

One notable obstacle to the use of particles for the separation and subsequent release of distinct, selected subsets from a mixed population of biological entities is that the biological entities must be collected in such a manner as to allow the selected subset to be removed from the mixed population without appreciable contamination from non-selected substances. In the practice of the present invention, this difficulty is overcome in either of two ways. One is the high degree of control that is afforded over the collection of the biological entities, such that after an individual bonds between the biological entity and the solid support is cleaved, which may be either before or after resuspension of the collected biological entities, a second collection of the particles results in segregation of the original mixed population with the exception of the subset of biological entities that was bound by the specific receptor which was selectively released from its target subset via bond cleavage.

The second way involves depositing the captured biological substances in a substantially uniform thickness on a collection surface to minimize entrapment of non-bound or released substances. Relatively small receptor-coated magnetic particles may be advantageously used for this purpose, but other types and sizes of particles are not excluded. Preferred capture agents comprise receptors affixed to colloidal ferrofluids as described in U.S. Pat. No. 4,795,698 and in U.S. Patent Application Number 08/006,071 now U.S. Pat. No. 5,466,574, which are commonly owned with the present application, and which are incorporated by reference in the present application as if set forth herein in full. By the use of apparatus and methodology described in aforementioned U.S. Pat. No. 5,186,827 and Patent Application Number 08/006,071 now U.S. Pat. No. 5,466,574, it is possible to collect what is effectively a monolayer of the magnetic particles bound to captured biological entities. In a monolayer, after manipulation of the physicochemical environment, a released subset of a mixed population of biological entities can be recovered simply by washing the system with buffer. The formation of a monolayer of biological entities in this way is particularly effective in avoiding entrapment of non-bound substances.

A combination of both approaches may be utilized in cases when multiple subsets of biological entities are to be isolated from a mixed cell population which vary greatly in frequencies.

BRIEF DESCRIPTION OF THE DRAWINGS

In FIG. 1A, a mixed subpopulation of cell types B, C, and D is deposited on a collection surface, whereas the type A cell is removed with the fluid flow. In FIG. 1B, cell type D is selectively dissociated from its capture agent by disruption of the attachment between the receptor and the solid support.

FIGS. 4A and 4B illustrate the capture of a relatively large subpopulation from the original mixed population of cells and deposition on a collection surface. FIG. 4C represents the resuspension of the collected subpopulation. FIG. 4D illustrates the re-collection of the resuspended subpopulation after dissociation of the first capture agent and binding to a second capture agent, resulting in the capture and collection of a substantial portion of the subpopulation, with the exception of the target subset of interest which is selectively released.

DETAILED DESCRIPTION OF THE INVENTION

Figure 1A:
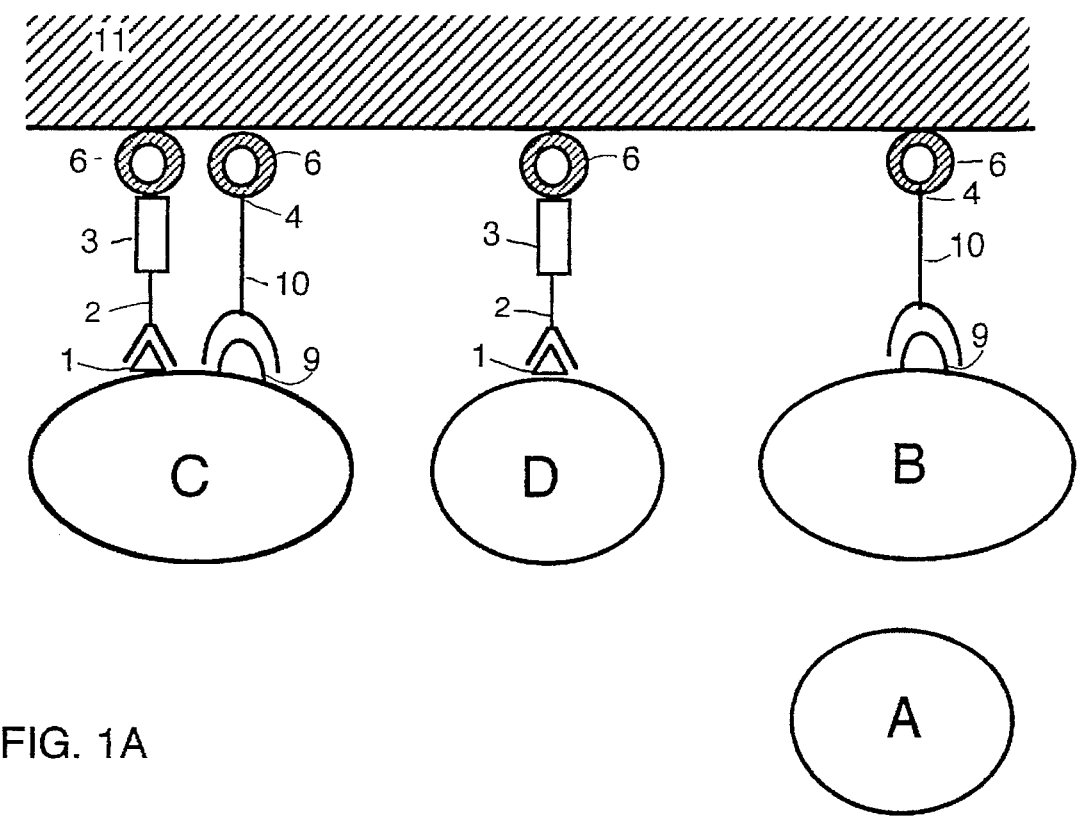
FIGS. 1A–B illustrates the separation of a mixture of four different cell types into three separate subsets, i.e., A, D, and B/C.

The separation method of the invention employs a unique combination of steps to capture a mixed population of biological entities and to release therefrom selected entities of interest.

This method enables the efficient isolation of a broad range of biological entities, which may be a component of a test sample or specimen capable of selective interaction with a receptor or other specific binding substance. The term "biological entity" as used herein refers to a wide variety of substance of biological origin including cells, both eukaryotic (e.g., leukocytes, erythrocytes or fungi) and prokaryotic (e.g., bacteria, protozoa or mycoplasma), viruses, cell components, such as organelles, vesicles, endosomes, lysosomal packages or nuclei, as well as molecules (e.g., proteins) and macromolecules (e.g., nucleic acids—RNA, DNA).

The biological entities of interest may be present in test samples or specimens of varying origin, including, without limitation, biological fluids such as whole blood, serum, plasma, bone marrow, sputum, urine, other bodily fluids, such as cerebrospinal fluid, amniotic fluid or lavage fluids, as well as tissue homogenates, disaggregated tissue or cultured cells.

The term "determinant" is used here in a broad sense to denote an element that identifies or determines the nature of something. When used in reference to any of the above-described biological entities, "determinant" means that portion of the biological entity involved in and responsible for selective binding to a specific binding substance, the presence of which is required for selective binding to occur. The expression "characteristic determinant" is used herein in reference to cells, for example, signifies an epitope (or group of epitopes) that serve to identify a particular cell type and distinguish it from other cell types. Cell-associated determinants include, for example, components of the cell membrane, such as membrane-bound proteins or glycoproteins, including cell surface antigens of either host or viral origin, histocompatibility antigens or membrane receptors.

The expression "specific binding substance" as used herein refers to any substance that selectively recognizes and interacts with the characteristic determinant on a biological entity of interest, to the substantial exclusion of determinants present on biological entities that are not of interest. Among the specific binding substances which may be used in affinity-binding separations are antibodies, anti-haptens, anti-lectins, peptides, peptide-nucleic acid conjugates, nucleic acids, Protein A, Protein G, concanavalin A, soybean agglutinin, hormones and growth factors. The term "antibody" is intended to include monoclonal or polyclonal immunoglobulins, immunoreactive, immunoglobulin fragments, as well as single chain antibodies.

Representative examples of characteristic determinants and their specific binding substances are hormone-receptor, ligand-receptor, agonist-antagonist, RNA or DNA oligomers-complimentary sequences, $F_c$ receptor of mouse $I_gG$-protein A, avidin-biotin and virus-receptor. These are sometimes referred to herein as "specific binding pairs". Other determinant-specific binding pair combination that may serve as a basis for affinity-binding separations in accordance with this invention will be apparent to those skilled in the art.

An affinity binding/cleavage pair is a functional chemical entity which has the following characteristics: (1) it can specifically bind to an antigenic determinant; (2) it is attached or can be specifically attached to a solid support; and (3) it has a site which can be specifically cleaved at a point between the surface of the antigenic determinant and the solid support, including specific modifications to the antigenic determinant which will also result in cleavage.

The capture agents used in carrying out the method of the invention comprise a specific binding agent, or receptor, attached to a solid support. The solid support may be either stationary or mobile, the latter being preferred. Suitable stationary solid supports include, without limitation, microtitre plates, test tubes, membranes and filter media, e.g., filter paper. Useful mobile solid phases include, without limitation, inorganic particulate materials, organic particulate materials and organic-inorganic composite particulate materials. Particulate solid supports are preferably made from magnetic material to facilitate capture of the target subsets.

A particularly preferred form of capture agent is a colloidal, magnetically-responsive material prepared by the co-precipitation of bioactive polymers e.g., proteins or polynucleotides, with certain transition metal salts. The procedure for the preparation of such capture agents is described in detail in the aforementioned U.S. Pat. No. 4,795,698. Capture agents produced in this manner may comprise various biologically active polymers, such as antibodies, enzymes, viral antigens, complement components, wheat germ agglutinin, nucleic acids and the like incorporated onto colloidal, magnetically responsive particles, while retaining native biological activity.

The instant invention enables the separation and collection of several target substances from a test sample en masse, followed by specific release of individual selected subsets by dissociating the selected subset from the capture agent to which it is bound. In order to maintain specificity of release during sequential separations, distinct mechanisms for dissociating each selected subset from its respective capture agent are required. Various mechanisms are available to accomplish the dissociation required to release the selected target from its capture agent. Enzymatic cleavage, restriction enzymes, detergents, or chemically-induced cleavage, to name a few, may be used in such a manner as to cause disruption of the specific receptor-solid support attachment, without detrimental effect on the viability or function of the target biological entity. Labile chemical bonds, hydrogen bonds, receptor configuration and other non-covalent interactions which may be used effectively to form the capture agents are sensitive to changes in pH, ultraviolet light, dielectric constant of the sample medium, ionic strength, or temperature. Additionally, the capture of target entities will enable the control of the sample volume.

Also contemplated to be within the scope of this invention is dissociation of a capture agent from its target subset by disrupting the attachment between the specific receptor and the determinants of the biological entities comprising the target subset to which the receptor binds. Some mechanisms that may be used to this end include disruption of the ligand-receptor interaction with calcium, nickel, gadolinium, as well as with various ions or chelating agents, or by competitive binding. See, for example, Friedman, ed., *Protein-Metal Interactions,* Chapter 9 (1974). Other alternative mechanisms include the specific, partial disruption of the solid support, which would allow the biological entities to be released from their captured state, or the disruption of a specific receptor-secondary specific receptor interaction.

The simplest application of the instant invention for the affinity-binding capture and subsequent release of selected biological entities is schematically illustrated for cell applications in FIG. 1A. A mixture of four different cell types A–D can be separated into three distinct subsets when bound to capture agents comprising two antibodies 2, 10 having different binding specificity which are bound through two different linkages 3, 4 to their solid supports 6, e.g., ferrofluid. Cell type A lacks the presence of ligands 1, 9 for both antibodies 2, 10, whereas cell types B and D each have one of ligand 1 or 9 for one of the two antibodies 2, 10. Cell type C has both ligands 1, 9.

After specific binding of the capture agents, the cells A–D are exposed to a high gradient magnetic field as described in U.S. Pat. No. 5,186,827. The cells B, C, D which specifically bind antibodies 2 and 10 are thereby deposited, preferably as a monolayer, on a collection surface. Cell type A, which is not bound to a capture agent is removed from the separation vessel for collection or disposal. Exposure to a physicochemical condition which releases the attachment 3 between the antibody 2 and its solid support 6 will result in the release of one of the four cell types.

Figure 1B:
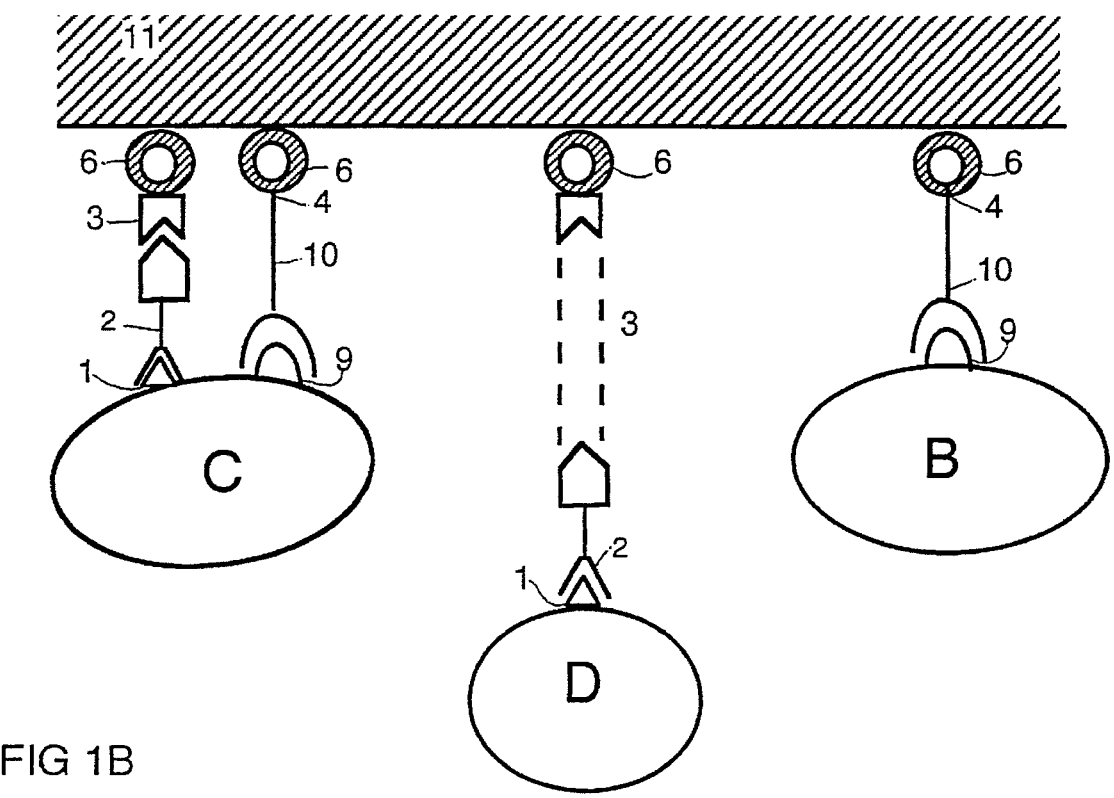
Figure 3A:
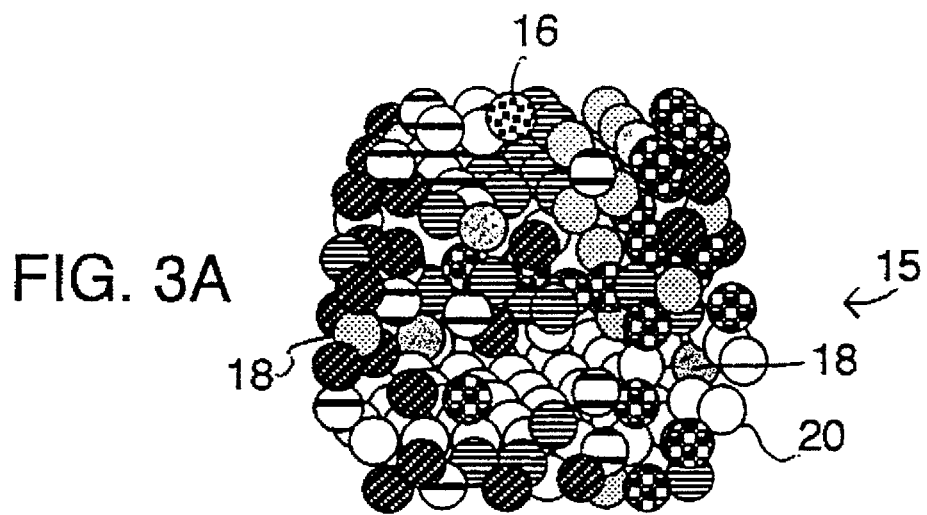
FIG. 3 illustrates the selection of a relatively small sub-population of cells from a larger mixed population of cells, with release of a distinct, selected subset of cells from a monolayer deposited on a collection surface.
Figure 3B:
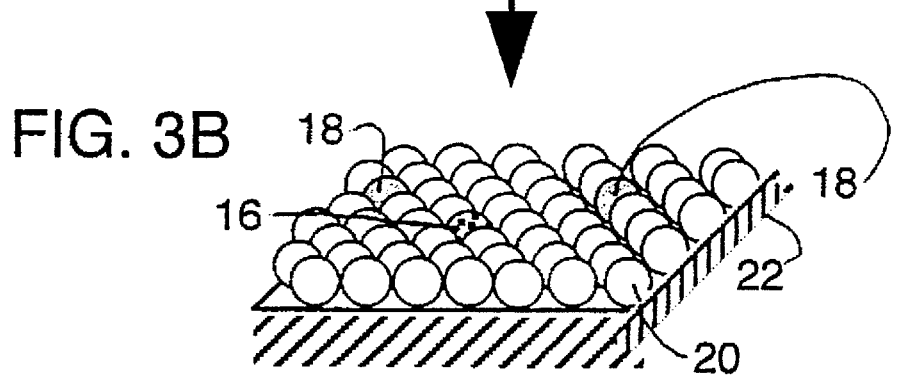
Figure 3C:
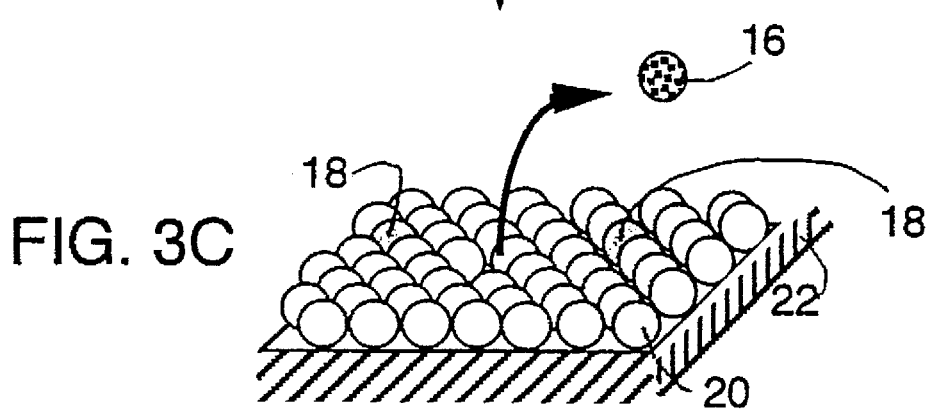
Figure 4A:
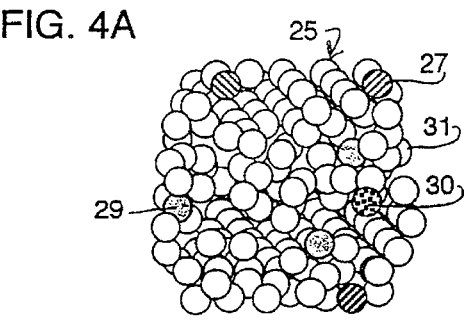
FIGS. 4A–D illustrate the selection of a distinct, selected cell subset from a large, mixed population of cells.
Figure 4B:
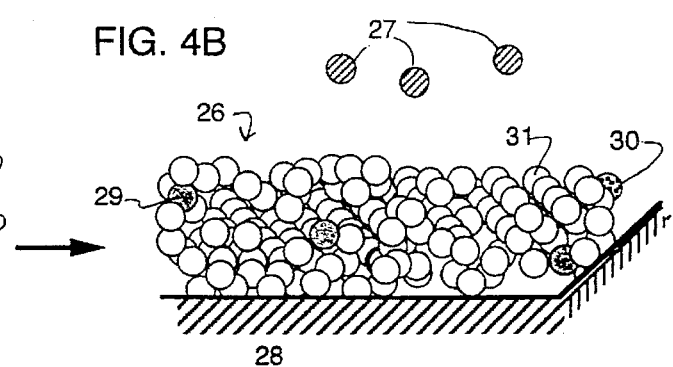
Figure 4C:
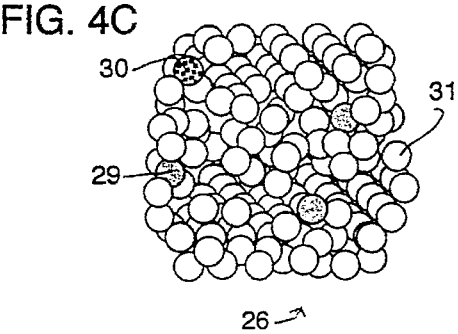
Figure 4D:
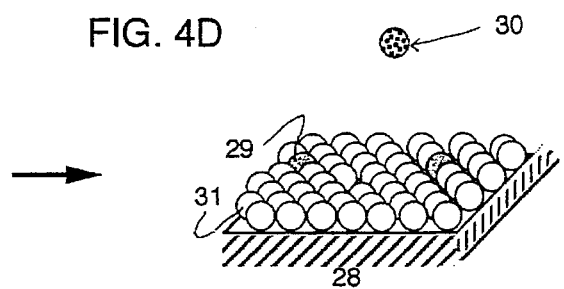

As shown in FIG. 1B, the antibody 2, which immunospecifically recognizes cell type D, is selectively dissociated from the ferrofluid by dissociation of bond 3 resulting in the selective release of cell D from the monolayer and subsequent removal from the vessel for collection. Although cell type C also has a ligand 1 in common with cell type D, it will remain captured through its interaction with antibody 10, because attachment 4 is not disrupted by the change of the physicochemical conditions that resulted in the release of cell type D. Therefore cell types C and B will remain bound. A similar separation technique is represented in FIGS. 3A–C. FIG. 3a illustrates an initial mixed cell population 15 including a distinct subset of interest, of which cell type 16 is typical. After incubation with capture agents comprising specific receptors bound to solid supports (not shown), the captured cells types 16, 18, 20 are deposited in a monolayer on a collection surface 22, as illustrated in FIG. 3b. After manipulation of the physical or chemical environment of the system, the cell type 16, and other cells of the same type, are selectively dissociated from capture agent and isolated from the collection surface 22 as shown in FIG. 3c. The other subsets in the population, such as cells types 18 and 20, remain in place on the collection surface 22.

In an alternative embodiment, it is envisioned that an initial separation step would be included before the protocol described above. This initial separation step may remove up to 90% of the cells in the initial population. This alternate separation protocol could be utilized in the event one of the cell types of interest is characterized by having two antigens, one of which is extremely common. In this case, it is possible to positively select a large cell subpopulation which is known to be of no interest. Thus, after removal of the large population, one could perform the separation method on the remaining population as taught above.

In another alternative embodiment, it is possible to perform an initial separation to positively select and collect a small (<5%) mixed population that includes the desired cell type (A). The non-selected cells, which do not include the type (A) of interest are then removed from the test medium. After the non-selected cells have been removed, the initially-collected population can be further separated by addition of various other specific receptors dissociably linked to capture agent. Then the initial capture agent can be released, by breaking the attachment between the initial capture agent and its solid support, thus allowing collection of the isolated desired subset.

As schematically illustrated in FIG. 4 (A and B), it is possible to select initially a large, mixed subpopulation 26 from an initial population 25, using a first receptor to the cell types in population 26, in order to remove undesired cell type(s) 27. The deposit of subpopulation 26 upon the collection surface 28 is not necessarily monolayered. Resuspension of the large, mixed subpopulation 26 can then be performed, as shown in FIG. 4C. After resuspension of the population 26, a second specific receptor may be added in addition to that already bound to the cells in subpopulation 26. Then, the subpopulation 26 is again collected upon the collection surface 28. After manipulation of the physicochemical environment in order to break the attachment between the first receptor and its solid support, a distinct subpopulation 30 of biological entities is freed, and can be collected in a fluid flow. It is also important to note that the manipulation of the physicochemical environment to release the distinct population 30 can be performed at any time before, during or after the incubation with the second set of specific receptors or after the second collection of the mixed biological entities. The population of cells remaining bound upon collection surface 28 after selective release of distinct population 30 may be "pure" or may contain at least one other distinct population 29.

In an alternative embodiment of the invention, the initial separation of biological entities may be accomplished by using one type of solid support in the initial separation and of a different type of solid support in the subsequent separation, e.g., a stationary support and a mobile support. One example might be the selection of approximately 1% of cells from peripheral blood using monoclonal antibody immobilized in a microtiter well. After separation and removal of unbound cells, a competitive ligand might be added to the microtiter wells, to remove the cells from the wall of the well. Then a second incubation with magnetic microspheres bound to several monoclonal antibodies, each in a unique, labile manner would be possible. Magnetic collection of the cellular suspension would result in the binding of all cells except those without antigenic determinants recognized by the magnetically labeled antibodies. Manipulation of the physicochemical environment would result in further separations of cellular sub-types.

A limited numeric analysis of the possible permutations of the methods disclosed herein is provided in Table I. For one antigen/specific receptor binding pair, the separation into distinct populations is a common procedure. However, for two of more antigenic sites, the advantages of the method of the invention become apparent. For example, for two determinants, the number of permutations is $2^2$, or 4. These include for antigens A and B, A–B–, A+B–, B+A–, and A+B+. The number of resulting distinct subsets is equal to the number of determinants plus one, as the dissociation of each specific capture agent will yield one distinct population, with an additional subset comprising cells devoid of the ligands to which the capture agents specifically bind. The separation of a mixture of four cell types having two characteristic determinants is described above with reference to FIG. 1.

TABLE 1

| No. of determinants | 1 | 2 | 3 | 4 | 5 |
|---|---|---|---|---|---|
| No. of antigenic combinations | 2 | 4 | 8 | 16 | 32 |
| No. of distinct populations | 2 | 3 | 4 | 5 | 6 |

Figure 2A:
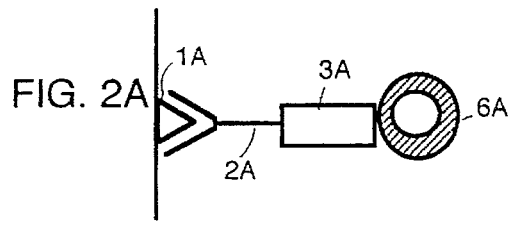
FIGS. 2A–E is a schematic representation of five different types of selective dissociation techniques. These include breakage of attachment between solid support and specific receptor (FIG. 2A); release of ligand by specific receptor (FIG. 2B); degradation of the solid support (FIG. 2C); disruption of a secondary attachment such as an auxiliary capture agent (FIG. 2D); or digestion of the cell surface antigen (FIG. 2E).
Figure 2A:
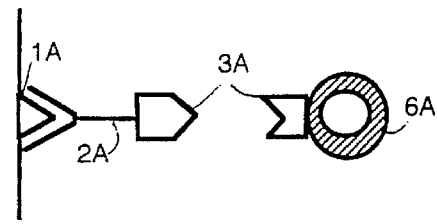
Figure 2B:
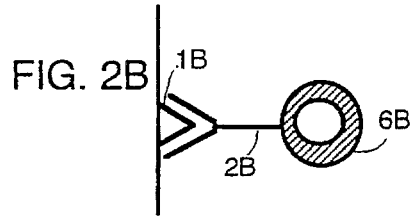
Figure 2B:
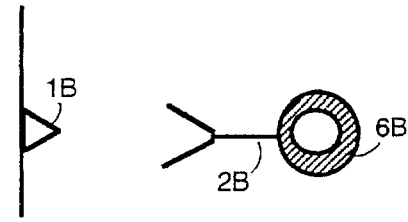
Figure 2C:
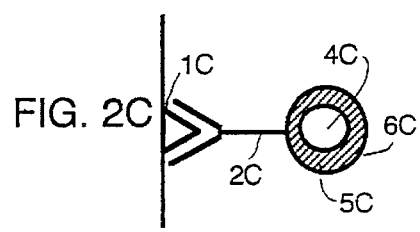
Figure 2C:
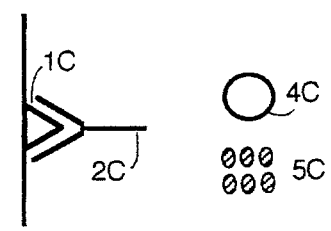
Figure 2D:
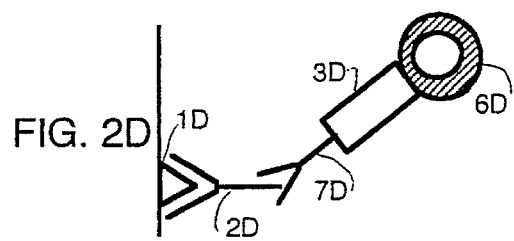
Figure 2D:
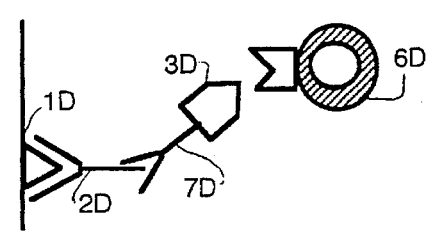
Figure 2E:
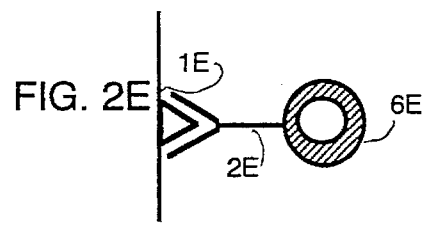
Figure 2E:
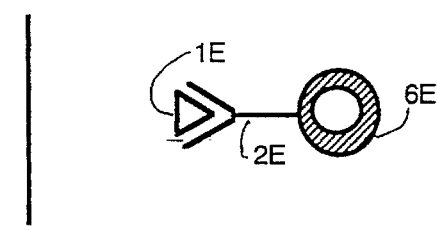
Figure 2E:
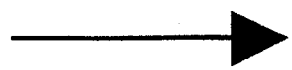

Several criteria have been found to be desirable in the practice of the methods disclosed herein. For example, the biological entities to be separated must have distinct sites recognizable by specific receptors. Also, the biological substances should be adapted for collection in such a manner as to allow non-bound substances to be removed from the system with minimal entrapment thereof. Additionally, it is desirable to provide a linkage between the biological substances and a solid support which can be broken upon the application of specific changes in the physicochemical environment. This breakage can be at any point between the biological substance and the solid support as is illustrated in FIGS. 2A–E. In FIG. 2A, the linkage 3a between the specific receptor 2a and the solid support 6a is broken. In FIG. 2B, the linkage between the ligand 1b and the specific receptor 2b is disrupted, freeing solid support 6b, which remains attached to receptor 2b. In FIG. 2C, the solid support 6c is disrupted into component parts 4c and 5c leaving specific receptor 2c bound to ligand 1c. In FIG. 2D, the linkage 3d between the solid support 6d and the secondary specific receptor 7d is broken in this case also leaving specific receptor 2d bound to ligand 1d. In FIG. 2E, the ligand 1e is cleaved from the biological entity 8e and remains bound to specific receptor 2e, which is attached to solid support 6e.

Some of the molecular manipulations that may be employed to provide selective breakage of binding links between ferrofluid-bound receptors and their associated ferrofluid supports have been described hereinabove. For example, a specific receptor such as an antibody could be linked to the solid support via a relatively short nucleotide sequence. If a nucleotide sequence of a 6-mer of poly-A could be covalently coupled to the solid support, while the complementary 6-mer of poly-T could be covalently coupled to the antibody, the antibody could bind to its antigen, the solid support/antibody/antigen complex could be separated, and then by merely raising the temperature, the hydrogen bonds between the two nucleotide sequences could be broken, releasing the antibody-antigen complex from the solid support. Obviously, it is unimportant which of the nucleotide strands were attached to the antibody and which to the solid support. Another possibility is if a nucleotide sequence were used to link the solid support to the antibody, similarly to as described above and the polynucleotide was of a proper sequence, length and steric environment, a restriction enzyme could be used to cleave the polynucleotide, again releasing the antibody from the solid support.

Other means of release might involve chemical cleavage of a susceptible bond such as dithiothreitol or beta-mercaptoethanol treatment of a disulfide. Labile esters, amides, and other linkages could be cleaved by temperature, chemicals (such as hydroxylamine), light, or pH manipulation. Linkage of the specific receptor to the solid support may be cleaved under the influence of electric charge. Enzymatic cleavage is another candidate for specific release of the biological entity but can only be used when it does not destroy the target biological entity. DNase or RNase used at a low level would digest a piece of DNA or RNA used as a "rope" to tie together the specific receptor and the solid support. A large variety of other enzymes are available which target intracellular substrates or extracellular substrates. Such substrates can be used as part of the linkage and can be dissolved by the enzymes specific for the substrate. Enzymes for proteins such as collagen, vimentin, elastin, desmin and laminin are readily available and large variety of enzymes can be obtained from commercial sources.

Also encompassed in this invention is the breakage of the specific receptor-ligand interaction. One possibility here would be the use of certain antibodies, which bind only in the presence or absence of calcium or other ions. Manipulation of these ions in solution or the use of chelating agents such as EDTA, EGTA, or DTPA would specifically disrupt these interactions. Other agents can induce conformational change in the specific receptor or other biological molecules used in the separation, which could cause the disruption of a non-covalent interaction. Ionic strength, dielectric constant, pH, and temperature are key parameters that could be manipulated. Competition for the binding site was used by Kessler (WO 94/02016) to displace biotin/anti-biotin interactions with biotin analogs. Excess amounts of free specific receptor can also displace a bound specific receptor/ solid support complex. Yet another approach is to alter the affinity of the specific receptor; a low affinity receptor is used to capture the biological entity and a high affinity receptor with the same specificity is used to compete with the low affinity receptor resulting in the release of the biological entity. An example of such alteration is to label an antibody with a certain specificity with a hapten such as biotin to such extent that it lowers the affinity of the antibody. Unmodified antibody would then be added to displace the modified antibody bound to the solid support, thus releasing the biological entity. In another embodiment of the invention, it can be foreseen that in certain instances, such as in diagnostics applications, a viable biological entity is not an important goal. In these cases, full or partial digestion of the ligand is a possibility.

With all of these types of chemical linkages that are intended to be disrupted in the practice of the invention, it is important to the instant invention that a combination of compatible chemistries are used. Sequential release requires that a mixed population of biological entities are collected, then one by one, distinct populations are released upon serial changes of the physicochemical environment. Finally, it is important to note that at least one of the linkages need not be labile. For a distinct population that one does not intend to release, specific receptors can be used that are not released under the conditions used in performing the method.

A final class of controlled release is applicable only with the use of magnetic beads and it would include the manipulation of the magnetic field with respect to particles with different magnetic susceptibilities. If one type of specific receptor were bound to a highly magnetic bead, and another type of specific receptor were bound to a bead with a low magnetic saturation, separation in a high gradient magnetic (HGMS) field would capture both types of beads. Removal from the HGMS field to a weaker magnetic separation device would result in the specific retention of biological substances bound to the highly magnetic beads, and the specific release of the biological substances bound to the bead with the low magnetic saturation. Greater resolution of subpopulations may be possible with this type of magnetic collection as no breakage of linkages actually occurs.

However, combinations where linkages are broken with downstream HGMS would allow for further collection and therefore, separation.

The following examples are provided to illustrate further aspects of the invention. Although the use of the methods of the invention are exemplified herein by the separation of rare cell populations, it will be apparent to those of skill in the art that the methods may also be used for other affinity-binding separations according to the same general procedures. These include, but are not limited to, the separation of various bacteria and parasites from fecal matter, urine, other bodily fluids, tissue homogenates, sludges, slurries, and water (e.g. ground water or streams); or in the separation of various bacteria, toxins, fungi or other target substances from food products or other sources.

EXAMPLE 1

The Linkage of a Specific Receptor to a Solid Support Such That the Receptor is Released Upon of the Physicochemical Environment A streptavidin ferrofluid is manufactured as described in U.S. patent application Ser. No. 397,106. It can be incubated with a (5') biotinylated poly-A chain of a 6-mer oligonucleotide (Midland Certified Reagent Co., Midland, Tex.) resulting in the ferrofluid bearing the poly A oligonucleotide. The complementary poly-T chain of the nucleotide can than be covalently attached to an antibody via a heterobifunctional linkage. The antibody would first be activated with N-succinimidyl-4-(N-maleimido methyl) cylcohexane-1-carboxylate (SMCC)(Pierce, Rockford, Ill.). Then the activated antibody would be reacted with a (3') thiolated poly-T chain of a 6-mer (Midland Certified Reagent Co., Midland, Tex.). The antibody and the ferrofluid would then be incubated together at a temperature sufficient to ensure the complete annealing of the two 6-mers.

The above method of linkage for an antibody with a ferrofluid could be repeated with 8-mers, 10-mers, and 12-mers. Each linkage would be with a different antibody. The ferrofluids with the different antibody linkages could be mixed, then incubated with a cellular suspension at 4° C. to promote binding of the target cells to the capture agents. After binding, the cell-bound capture agents could be collected on a surface of a magnetic flow through chamber as described in U.S. Pat. No. 5,186,827. The cell-bound capture agents would be collected substantially in a monolayer at 4° C. Then the entire apparatus could be warmed to 12° C. This step would disrupt the hydrogen bonds between the 6-mers of the poly A and poly T, and one antibody would be freed from the ferrofluid. Buffer at the same temperature would be washed through the system, collecting those cells that were released from the monolayer. Then the entire apparatus would be heated to 16° C., and the procedure repeated to release the antibody linked to the ferrofluid via the 8-mer. The entire process would be repeated at 20° C. and 24° C., each step releasing a different distinct subset of cells.

EXAMPLE 2

Simultaneous Isolation of Hematopoietic Progenitor Cells and Depletion of Malignant Cells In Patients With B-lymphoid Malignancies Human blood or bone marrow cells are incubated with two monoclonal antibodies having two different specificities; (1) anti-CD34 antibodies that specifically bind hematopoietic progenitor cells, which cells are present in a frequency of approximately 1% in human bone marrow and (2) anti-CD19 antibodies which specifically bind hematopoietic cells differentiated into the B-lymphoid lineage, among which is a population of early B-lymphoid cells which co-expresses CD34 and CD19. B lymphocytes are present in a frequency of approximately 5% in human bone marrow. The antibody recognizing CD34 is identified by a monoclonal antibody which is bound to a ferrofluid in such a way that the antibody can be released by a specific change in the physicochemical environment. In this embodiment, the binding of the specific receptor takes place at room temperature and the monoclonal antibody identifying CD34 is released from the ferrofluid at a temperature of 37° C. The cells incubated with the antibodies and ferrofluid are now exposed to a magnetic field. The cells labeled with antibody/ ferrofluid complexes are captured as a monolayer, whereas the cells not labeled with the antibody/ferrofluid complexes will be passed through the system and can be collected or disposed of as illustrated schematically in FIG. 3. The monolayer of cells significantly reduces the entrapment of non target cells and permits the release from a subpopulation of targets while captured. The captured cells constitute approximately 6% of bone marrow cells and comprise normal CD34+, CD19– progenitor cells; CD34+, CD19+ progenitor cells which contain normal as well as potentially malignant B cell progenitors; and CD34–, CD19+ normal as well as potentially malignant B lymphocytes. In addition, a portion of bone marrow cells will be labeled non-specifically and captured. Increase of the temperature will result in the breakage of the bond between the CD34 antibody and the ferrofluid and will result in the release and collection of CD34+ cells which do not express the CD19 antigen. The remaining non-specifically captured cells and CD19+ captured cells can be released subsequently by taking the separation chamber out of the magnetic field and analyzing for the proportion and number of malignant cells. An approach which would lead to superior depletion is to first deplete the sample from CD19-bearing cells using this or other affinity separation technology, followed by the steps described above, using an anti-CD19 antibody which specifically binds an epitope different from that bound by the anti-CD19 antibody first described above.

EXAMPLE 3

Isolation of Hematopoietic Stem Cells, Hematopoietic Progenitor Cells and Depletion of Malignant Cells In Patients With B-lymphoid Malignancies In blood cell and bone marrow transplantation it is important that the graft contains a sufficient number of hematopoietic stem cells and hematopoietic progenitor cells to engraft in the fastest possible manner. Of equal importance is that in autologous transplantation for malignancies the majority if not all tumor cells should be eliminated. To achieve the greatest level of tumor cell depletion in B cell malignancies a first round of selection of progenitors cells will deplete a large proportion of B lymphoid cells; and a second round would involve the specific capture of any residual cell committed to the B cell lineage. Sequential separation of selected cell subsets from a mixed cell population may be achieved by incubating blood or bone marrow cells at room temperature with an antibody that specifically bind CD34, which can be released from the ferrofluid at a temperature of 37° C. The cell-bound capture agents are collected by exposure to a magnetic field while all other cells remain unbound and can be collected or disposed of, as desired. The separation chamber is now removed from the magnetic field and the cells are exposed at room temperature to two antibodies. The second antibody specifically binds CD38 a determinant of activated lymphoid cells, plasma cells, myeloid cells and CD34+ cells which are differentiated into one of the hematopoietic cell lineages and comprise approximately 25% of human bone marrow cells and >90% of the CD34+ cell fraction. The third antibody specifically binds CD19 which is a determinant of all B lymphocytes. The anti-CD38 antibody is released from the ferrofluid at a temperature of 4° C. In this example it would be desirable to select/collect hematopoietic stem cells defined as CD34+, CD38−, CD19−, and normal hematopoietic progenitors defined as CD34+, CD38+, CD19−. Any CD34+, CD38+, CD19+ cells; CD34+, CD38−, CD19+ cells or nonspecifically bound or entrapped cells would remain captured. After incubation the temperature is increased to 37° C. and the attachment between ferrofluid and CD34 is disrupted and the cells are exposed again to the magnetic field. Cells which express CD34 but lack both CD19 and CD38 are not captured, whereas all other CD34+ cells are recaptured. Decrease of the temperature to 4° C. will result in the release of the CD34+ cells which express CD38 but not CD19.

EXAMPLE 4

Isolation of Genetically Modified Hematopoietic Stem Cells and Depletion of Malignant Cells of Non-Hematopoietic Origin A cell suspension containing hematopoietic progenitor cells is manipulated in an attempt to genetically modify the early hematopoietic progenitor cells. The vector used contains not only the genetic material to be transferred for obtaining the desired therapeutic effect but also genetic material (referred to herein as Gene) that codes for a cell surface determinant which can be specifically identified with a probe. The method described herein would permit the identification and isolation of the transduced hematopoietic progenitor cells. The cell suspension is incubated with a monoclonal antibody that specifically binds hematopoietic progenitor cells (such as CD34), a monoclonal antibody which is present on lineage committed but not uncommitted progenitor cells (such as CD38) and the probe identifying the cell determinant indicating a successful transduction (Gene). The antibody that binds hematopoietic progenitor cells is attached to its particulate solid support in such way that the attachment will be disrupted at 37° C. The probe identifying the cell determinant is attached to the separation particle in such a way that the attachment will be disrupted at 4° C. After incubation with the cell-bound capture agents are exposed to a magnetic field. The bound cells are captured as a monolayer, whereas the unbound cells will pass through the system and can be collected or discarded. Increase in temperature to 37° C. results in the release of the progenitor cells which are not transduced (CD34+, CD38−, Gene−). Decrease in temperature to 4° C. results in the release of hematopoietic stem cells which are transduced (CD34+, CD38−, Gene+ and CD34−, CD38−, Gene+). An alternative protocol would involve the capture of the CD34+ cells followed by the release and capture of Gene+ and CD38+ cells and subsequent release thereof. It is obvious to one skilled in the art that any combination of receptors can be used and their use is solely dependent upon the specific goals required for the application. Also, various combinations of capture, and dissociation of capture agent from target subset may be used. For example magnetic capture/magnetic release/bond release/magnetic capture/bond release.

EXAMPLE 5

Isolation of Fetal Nucleated Erythrocytes from Maternal Blood

Maternal blood can be incubated with CD45, CD71 and HLA-G, each bound to a magnetic particle by a different dissociation mechanism. The expression of CD45 is restricted to leukocytes of both fetal and maternal origin. The expression of CD71 is restricted to nucleated red blood cells and proliferating or activated leukocytes (of fetal and maternal origin). The expression of HLA G is restricted to cells of fetal origin. All leukocytes and cells expressing CD71 and HLA-G can be captured. The attachment binding CD71-bearing cells to their capture agent can then be disrupted, thus releasing CD71+, CD45−, HLA-G− cells (maternal nucleated erythrocytes). Next, the attachment binding HLA-G-bearing cells to their capture agent can be disrupted, thus releasing HLA-G+, CD71+, CD45− cells and HLA-G+, CD71−, CD45− cells (fetal nucleated erythrocytes and other fetal non leukocytes such as trophoblasts).

Sequential separation of selected cell subsets from a mixed cell population in the manner described below enables the selection of infrequent cell populations notwithstanding that no specific markers are available for such cells. In the case of nucleated erythrocytes one can combine cell surface antigens which recognizes the majority or all leukocytes but not nucleated erythrocytes (such as CD11a/18, CD43, CD45, CD46, CD50) with antigens which identify a large proportion of cells including most leukocytes excluding nucleated erythrocytes (such as CD44, CD55, CD59) or cell surface antigens which recognize a smaller proportion of cells including nucleated erythrocytes (CD17, CD36, CD48, CD71). The antibodies which recognize nucleated erythrocytes are dissociably attached to a ferrofluid, whereas the antibody that specifically bind cell subsets not including nucleated erythrocytes are attached to ferrofluids by standard means. The cell population is incubated with the capture agents and the bound cells are collected by magnetic separation. The magnetic field is then removed and consequently the cells are released. The cells are next exposed to a physicochemical environment which breaks the bonds of the antibody which specificity includes nucleated erythrocytes. Thereafter, the cells are now exposed again to the magnetic field and all cells which are bound by the antibody that specifically binds all but nucleated erythrocytes are recaptured.

Optionally, the cells may be exposed to 0.17M $NH_4Cl$ (ammonium chloride) or low pH citrate phosphate to differentially lyse the erythroid of maternal origin.

The usage of a variety of enzymes which are present at different concentrations in erythroid cells of fetal and maternal origin can be used to reduce the number of maternal cells or differentiate between the fetal and maternal cells. To visualize the cells, use of a substrate which changes color in the presence of the enzyme would differentiate between fetal and maternal cells. To reduce the number of maternal cells, interference of the function of the enzyme will result in cell deterioration and cell death. Enzymes which would be useful in this type of visualization/differentiation include, but are not limited to hexokinase, trisophosphate isomerase, phosphoglycerate kinase, enolase, pyruvate kinase, lactate dehydrogenase, glucose-6-phosphate dehydrogenase.

The nucleated erythrocytes are, however, not captured and are recoveable for cell analysis, cell culture or genetic analysis, as desired.

EXAMPLE 6

Isolation of Non-Hematopoietic Cells and Depletion of Hematopoietic Cells

The majority of cells in bone marrow, blood and lymph nodes are of hematopoietic origin which makes the identification and enumeration of cells of non-hematopoietic origin such as mesenchymal derived cells, epithelial cells and potential malignant cells of non-hematopoietic origin, extremely difficult. The simultaneous occurrence of two or more cell surface determinants which are broadly expressed can be used to isolate such cells when the cells of non-hematopoietic origin express only one of the two cell surface determinants. Labeling of cells with such receptors and the subsequent release of the receptor which is expressed on non hematopoietic cells will result in the isolation of cells of non hematopoietic origin regardless of the fact that the released receptor is also expressed on cells of hematopoietic origin. Examples of receptors expressed on leukocytes, platelets and erythrocytes are CD11a/18, CD17, CD36, CD41, CD42, CD43, CD45, CD46, CD50, CD61 and Glycophorin A. The simultaneous use of CD45, CD61 and Glycophorin A would, for instance, capture all cells of the hematopoietic cell lineages. Examples of receptors broadly expressed on the majority of cell types are Class I antigens or receptors which are present on a large variety of cell types including non-hematopoietic cells such as CD44, CD49b, CD49e, CD55, CD59 and receptors for cell surface matrix proteins. Protocols useful for isolating the cell types of non-hematopoietic origin are described in the previous examples.

EXAMPLE 7

Isolation and Enumeration of Selected Cell Populations of the Hematopoietic Cell Lineages Sequential separation of selected cell subsets from a mixed cell population in the manner described herein enables the identification and enumeration of cell populations for which no specific cell receptors are available but which can be identified using a combination of cell surface determinants. It is desirable, for instance, to identify the different stages of neutrophils during their development. Anti-CD33 monoclonal antibodies will specifically bind all cells committed to the myeloid cell lineage but is also expressed on non lineage committed hematopoietic progenitors and progenitors committed to the erythroid cell lineage. Anti-CD64 monoclonal antibodies bind both monocytes and neutrophils, but the expression of this surface antigen is down regulated late in neutrophil development. Anti-CD16 monoclonal antibodies bind not only cells in the last stage of granulocyte maturation but also identify natural killer (NK) cells. Likewise, CD10 is expressed only during the last stage of differentiation and is also expressed on B cell precursors. Anti-CD56 monoclonal antibodies bind NK cells. Anti-CD14 monoclonal antibodies bind monocytes. Capture agents for bone marrow or peripheral blood comprising antibodies to CD33, CD64, CD14, CD16 and CD56, for example, can result in the capture of all cells expressing at least one of these receptors. Disruption of the attachment between the CD33-bearing cells and their capture agent will result in selective release of cells which express CD33 but not CD64, CD14, CD56 and CD16. Disruption of the attachment between the CD64-bearing cells and their capture agent will result in selective release of the immature precursors of the neutrophil lineage. Disruption of the attachment between the CD14-bearing cells and their capture agent will result in the selective release of monocytes. Disruption of the attachment between the CD16-bearing cells and their capture agent will result in the selective release of mature granulocytes, whereas the NK cells remain bound. After each release of cells, the cells can be counted online by impedance (electronic volume), lightscatter, fluorescence, absorption, DNA content or colorimetric determination as they pass by in the fluid flow.

Another beneficial protocol involves the use of "dissociable" receptors that specifically bind CD3, CD4, CD8, CD19 and CD56. Cells bound by one or more of these receptors are first captured on a suitable support. The receptors are then dissociated and the released cells are subjected to further analysis. The further analysis may involve measurement of a variety of parameters, such as by impedance (electronic volume), lightscatter, fluorescence, absorption, DNA content or colorimetric determination. In this example, the dissociation of the CD19 receptor will result in the release of B lymphocytes, dissociation of the CD4 receptor will result in the release of monocytes, dissociation of the CD3 receptor will result in the release of CD4+ T-lymphocytes, disruption of the CD8 receptor will result in the release of CD8+ T-lymphocytes and the disruption of the CD56 receptor will result in the release of NK cells.

EXAMPLE 8

Graft Engineering For Transplantation

In order to produce a graft which is composed of a selective distribution of cell types it is desirable to have a technology which enables the isolation and enumeration of selected cell types from which the graft is derived. Although today the ideal composition is not yet known, the procedure for sequential separation of selected cell subsets from a mixed cell population as here described will enable to this goal to be achieved once the optimal composition is known. Most likely a composition of uncommitted hematopoietic progenitor cells, lineage committed hematopoietic progenitor cells, immunocompetent cells such as NK cells or T lymphocyte subsets are likely candidates. The availability of cell surface determinants which are present on the surface of the target cells will enable the sequential selective separation procedure to isolate each of the cell types and permit the creation of the optimal cell mixture thereafter as described in the examples above.

EXAMPLE 9

Capture of DNA and Subsequent Selective Release of DNA Recognized By Probes With Specific Sequences DNA and or RNA is isolated from human bodily fluids or tissue homogenates. A sequence conserved between species is used as a primer to amplify the DNA or RNA. The amplified sample is incubated with a variety of probes which are specific for individual species. Ferrofluid bound DNA/RNA is captured as a result the species specific DNA/RNA is purified. Each of the probes is attached to a ferrofluid which can be differentially dissociated by changing the physicochemical environment. Subsequent release and detection of the presence or absence of DNA/RNA after each release step is indicative of the species of interest.

While various aspects of the present invention have been described and exemplified above in terms of certain preferred embodiments, various other embodiments will be apparent to those skilled in the art.

For example, the methods, compositions and test kits of the invention may be used in conjunction with the multi-pole magnetic separator disclosed in U.S. Pat. No. 5,186,827, or with the multi-phase separation technique disclosed in U.S. patent application Ser. No. 08/228,818, filed Apr. 18, 1994. The disclosures of the last-mentioned patent and application are incorporated by reference to the present application as if set forth herein in full.

For the practice of the methods disclosed herein, it is expected that kits for the selection of specific biological entities for therapeutic or diagnostic purposes may be provided. For example, a kit for fetal cell isolation and analysis would include antibodies which recognize maternal leukocytes and nucleated red blood cells; a solid support, such as magnetic particles, having the antibodies attached thereto; reversible cleavage reagents for releasing at least one captured cell population; a reagent for distinguishing fetal erythrocytes from other cells (such as mRNA for HLA G which is linked to a fluorescent label); chromosome probes, having fluorescent labels, for chromosomes 21, 18,13, X and Y; and instructions for use of the kit in pre- or post-natal diagnosis or screening of fetal cells in maternal blood. Such a kit would be used in conjunction with a magnetic separation apparatus. Other kits using the methods of affinity capture with selective subset release would include kits for the diagnosis of cancer, leukemia, AIDS, or other infectious diseases, or for the detection of food-borne pathogens or toxins.

The method is, therefore, not limited to the embodiments specifically described and exemplified above, but is capable of variation and modification without departing from the spirit of the invention, the full scope of which is delineated by the appended claims.

What is claimed is:

1. A method for isolating a selected subset of biological entities from among a plurality of subsets in a mixed population of said biological entities, said biological entities being selected from the group consisting of cells, bacteria, viruses, or components thereof and toxins, said plurality of subsets comprising a first subset having a first characteristic determinant and at least one other subset having at least a second characteristic determinant, one of said first subset and said at least one other subset being said selected subset, said method comprising the steps of:

(a) providing a plurality of capture agents, each capture agent comprising a receptor attached to a solid support, said plurality of capture agents including a first capture agent comprising a receptor which specifically binds, either directly or indirectly, to said first characteristic determinant and at least one other capture agent comprising a receptor which specifically binds, either directly or indirectly, to said second characteristic determinant, the subset to which each said capture agent binds being its target subset;

(b) contacting a test sample comprising said mixed population of biological entities with said plurality of capture agents, whereby the receptor of said first capture agent specifically binds to said first subset and the receptor of said at least one other capture agent specifically binds to said at least one other subset, at least one of said first and said second capture agents being dissociably linked to its target subset;

(c) collecting on a collection surface the bound subsets from said test sample and separating from said bound subsets any subset of said population than is not bound to a capture agent;

(d) selectively releasing one dissociably linked target subset, among said bound subsets, from said collection surface by dissociating said one dissociably linked subset from all or part of the capture agent to which it is bound; and (e) isolating said selectively released target subset.

2. A method as claimed in claim 1, including the further step of recovering said isolated subset.

3. A method as claimed in claim 1, wherein said first or said second capture agent, bearing its target subset and remaining attached to its solid support after performing steps (a)–(e), is dissociably bound to its target subset, and said method further includes the steps of dissociating said remaining capture agent from its target subset and isolating the subset dissociated from said remaining capture agent.

4. A method as claimed in claim 3, including the further step of recovering said isolated subset dissociated from said remaining capture agent.

5. A method as claimed in claim 1, wherein the receptor of at least one of said first capture agent and said at least one other capture agent is selected from the group consisting of antibodies, anti-haptens, anti-lectins, peptides, peptide-polynucleotide conjugates, polynucleotides, Protein A, Protein G, concanavilin A, soybean agglutinin, hormones and growth factors.

6. A method as claimed in claim 1, wherein said capture agents are attached to a stationary solid support.

7. A method as claimed in claim 6, wherein said solid support is selected from the group consisting of a microtiter plate, test tube, membrane and filter medium.

8. A method as claimed in claim 1, wherein said capture agents are attached to a mobile solid support.

9. A method as claimed in claim 8, wherein said solid support is selected from the group consisting of inorganic particulate material and organic-inorganic composite particulate materials.

10. A method as claimed in claim 8, wherein said solid support is magnetically responsive.

11. A method as claimed in claim 10, wherein said bound subsets are collected in a substantially uniform thickness on said collection surface under the influence of a magnetic field, said magnetic field being substantially uniform at said collection surface and being stronger in said test sample adjacent to said collection surface than in the test sample which is distant from said collection surface.

12. A method as claimed in claim 11, wherein said bound subsets are deposited on said collection surface in a thickness which is about the size of said subset-bearing magnetic capture agent.

13. A method as claimed in claim 1, wherein each of said first capture agent and said at least one other capture agent is in the form of antibody-bound magnetic particles comprising a magnetic metal compound as said solid support and an antibody as said receptor.

14. A method as claimed in claim 1, wherein the receptor of at least one capture agent is chemically attached to its solid support.

15. A method as claimed in claim 1, wherein the receptor of at least one capture agent is attached to its solid support via a disulfide bond.

16. A method as claimed in claim 1, wherein the receptor of at least one capture agent is attached to its solid support via a polynucleotide linkage.

17. A method as claimed in claim 16, wherein said polynucleotide linkage comprises a recognition sequence for a site-specific cleaving agent.

18. A method as claimed in claim 14, wherein said capture agent is dissociated from its target subset by chemically disrupting the attachment between the receptor of said capture agent and its solid support.

19. A method as claimed in claim 1, wherein the receptor of at least one capture agent is adsorbed to its solid support.

20. A method as claimed in claim 1, wherein said capture agent is dissociated from its target subset by disrupting the attachment between the receptor of said capture agent and its solid support.

21. A method as claimed in claim 20, wherein said chemical disruption is effected by pH change.

22. A method as claimed in claim 20, wherein said disruption is effected by temperature change.

23. A method as claimed in claim 20, wherein said disruption is effected under the influence of electromagnetic radiation.

24. A method as claimed in claim 20, wherein said disruption is effected under the influence of electric charge.

25. A method as claimed in claim 20, wherein said disruption is effected by enzyme activity.

26. A method as claimed in claim 1, wherein the receptor of at least one capture agent is bound directly to its target subset, said receptor being directly or indirectly attached to its solid support.

27. A method as claimed in claim 26, wherein said capture agent is dissociated from its target subset by disrupting the attachment between the receptor of said capture agent and the determinant of the biological entities comprising said subset.

28. A method as claimed in claim 1, wherein the receptor of at least one capture agent is bound sequentially to its target subset by a specific-binding substance which specifically binds to the characteristic determinant of the target subset of said capture agent, the receptor of said capture agent binding specifically to said specific binding substance, said receptor being directly or indirectly attached to its solid support.

29. A method as claimed in claim 28, wherein said capture agent is dissociated from its target subset by disruption of the attachment between the receptor component and solid support of said capture agent.

30. A method as claimed in claim 1, wherein said mixed population of biological entities is pre-treated to increase the relative content of said selected subset in said population.

31. A method as claimed in claim 2, wherein the recovered cells are cultured.

32. A method as claimed in claim 4, wherein the recovered cells are cultured.

33. A method as claimed in claim 1, wherein said isolated biological entities are subject to analysis by an analytical procedure selected from the group consisting of cell counting, flow cytometry, hematological analysis, polymerase chain reaction (PCR), ligase chain reaction (LCR), image analysis, gene product amplification, message amplification, colorimetric analysis, isotope counting, enzyme-linked immunosorbent assay (ELISA), in situ hybridization, fluorescence in situ hybridization, fluorescent microscopy and light microscopy.

34. A method as claimed in claim 1, wherein said test sample is a biological fluid selected from the group consisting of blood, bone marrow, sputum, urine, or other bodily fluid, tissue homogenate, disaggregated tissue and cultured cells.

35. A method for isolating a selected subset of cells from among a plurality of cell subsets in mixed cell population in a blood sample, said plurality of subsets comprising a first subset having a first characteristic antigen and at least one other subset having at least a second characteristic antigen, one of said first subset and said at least one other subset being said selected subset, said method comprising the steps of:

(a) providing a plurality of capture agents, each capture agent comprising an antibody attached to a solid support, said plurality of capture agents including a first capture agent comprising an antibody which specifically binds, either directly or indirectly, to said first characteristic antigen and at least a one other capture agent comprising an antibody which specifically binds, either directly or indirectly, to said second characteristic antigen, the antibody of each of said first and at least one other capture agent being dissociably attached to its solid support and the attachment of antibody to solid support in said first capture agent being different from the attachment of antibody to solid support in said at least one other capture agent, the subset to which each said capture agent binds being its target subset;

(b) contacting said blood sample with said plurality of capture agents, whereby the antibody of said first capture agent specifically binds to said first subset and the antibody of said at least one other capture agent specifically binds to said at least one other subset;

(c) collecting on a collection surface the bound subsets from said test sample and separating from said bound subsets any subset of said population that is not bound to a capture agent;

(d) selectively releasing one dissociably linked target subset, among said bound subsets, from said collection surface by dissociating said one dissociably linked subset from all or part of its solid support;

(e) isolating said selectively released target subset; and (f) dissociating the receptor of the other of said first or at least one other capture agent from its solid support; and (g) isolating the subset that had been bound to said other capture agent.

36. A method as claimed in claim 35, wherein at least one of said isolated cell subsets is recovered.

37. A method as claimed in claim 36, wherein at least one of said recovered cell subsets is cultured.

38. A method as claimed in claim 35, wherein said first and second capture agents each comprise a monoclonal antibody attached to a particulate, magnetic solid support.

* * * * *